United States Patent [19]

Wilkes

[11] 4,005,496
[45] Feb. 1, 1977

[54] PROSTHETIC KNEE JOINT

[75] Inventor: Donald F. Wilkes, Albuquerque, N. Mex.

[73] Assignee: Hosmer/Dorrance Corporation, Campbell, Calif.

[22] Filed: June 13, 1975

[21] Appl. No.: 586,544

Related U.S. Application Data

[63] Continuation-in-part of Ser. No. 484,627, June 28, 1974, abandoned.

[52] U.S. Cl. .......................................... 3/27; 3/22; 3/29; 3/2
[51] Int. Cl.² ........................ A61F 1/04; A61F 1/08
[58] Field of Search .................................. 3/22–29, 3/2, 1.2, 21

[56] References Cited

UNITED STATES PATENTS

| 50,770 | 10/1865 | Lockwood | 3/23 |
|---|---|---|---|
| 1,431,292 | 10/1922 | Dilworth | 3/29 |
| 2,046,069 | 6/1936 | Greissinger | 3/29 |
| 3,351,955 | 11/1967 | Middleton | 3/22 |
| 3,723,997 | 4/1973 | Kolman | 3/27 |
| 3,731,323 | 5/1973 | Glancy | 3/2 |

FOREIGN PATENTS OR APPLICATIONS

| 828,292 | 1/1952 | Germany | 3/22 |
|---|---|---|---|
| 66,257 | 5/1969 | Germany | 3/27 |
| 1,221,778 | 2/1971 | United Kingdom | 3/27 |

OTHER PUBLICATIONS

"Human Limbs & Their Substitutes" by Klopsteg & Wilson et al., McGraw–Hill Book Co., Inc., 1954, pp. 499–502, relied upon.

*Primary Examiner*—Ronald L. Frinks
*Attorney, Agent, or Firm*—Burns, Doane, Swecker & Mathis

[57] ABSTRACT

A prosthetic knee joint having a femoral member and a tibial member each of which is provided with a bearing surface. The bearing surface of the tibial member supports the bearing surface associated with the femoral member such that flexion between the tibial member and the femoral member causes the respective bearing surfaces to roll relative to one another. Rollers, cam surfaces and guide slots are provided to ensure the retention of the proper relationship for this rolling contact between the tibial bearing surface and the femoral bearing surface. The knee joint includes a mechanical brake which produces a brake force that increased with flexure between the tibial member and the femoral member. The brake includes a resilient deformable element which transmits a brake applying force to a brake shoe which is operable along an axis generally perpendicular to the direction in which the force is applied. Hyperextension of the knee joint is mechanically limited and a torsion rod accommodates torsional motion between the knee joint and a lower leg to which it may be attached. The knee joint also includes a member which simulates the movement of the patella bone of a human knee.

34 Claims, 13 Drawing Figures

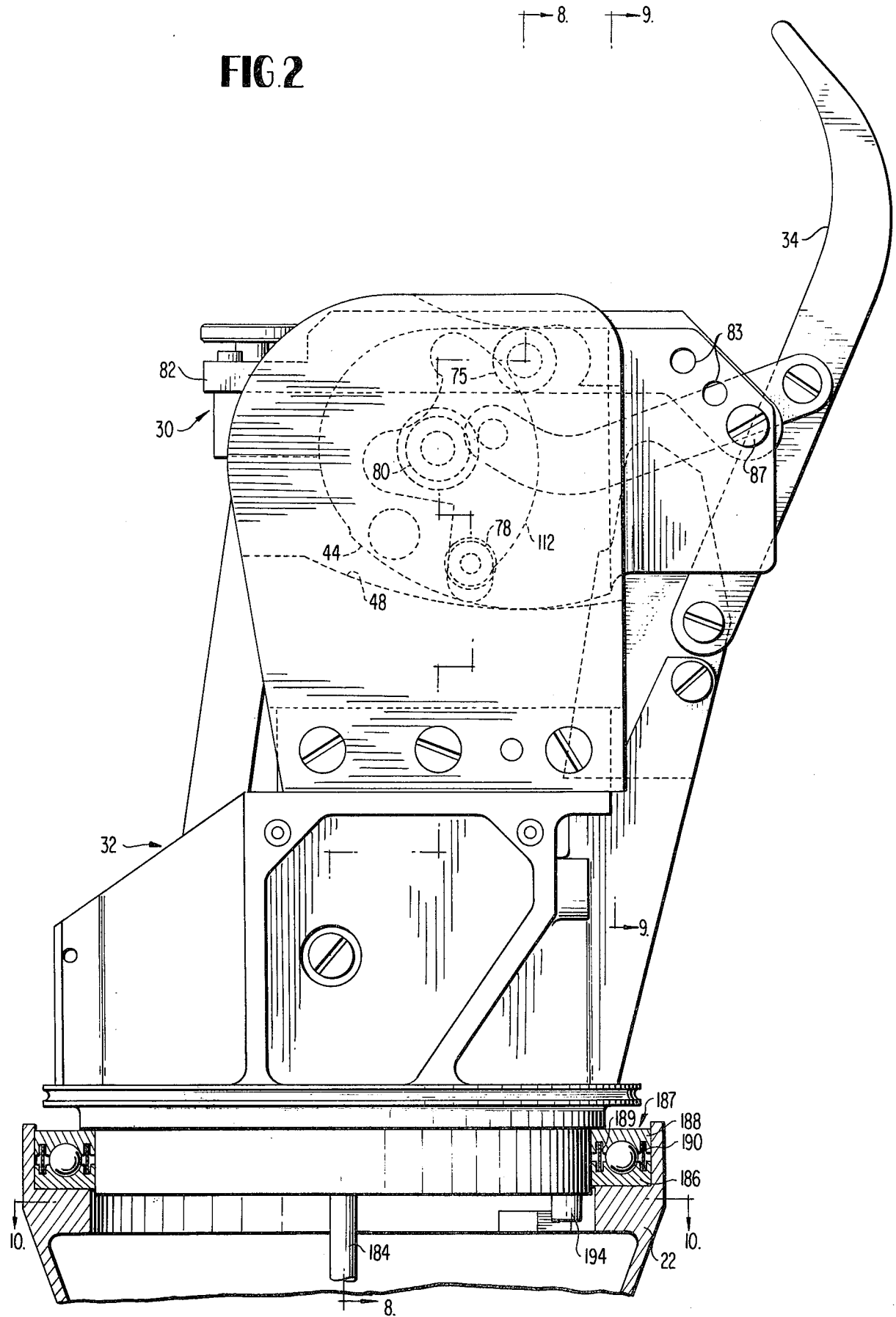

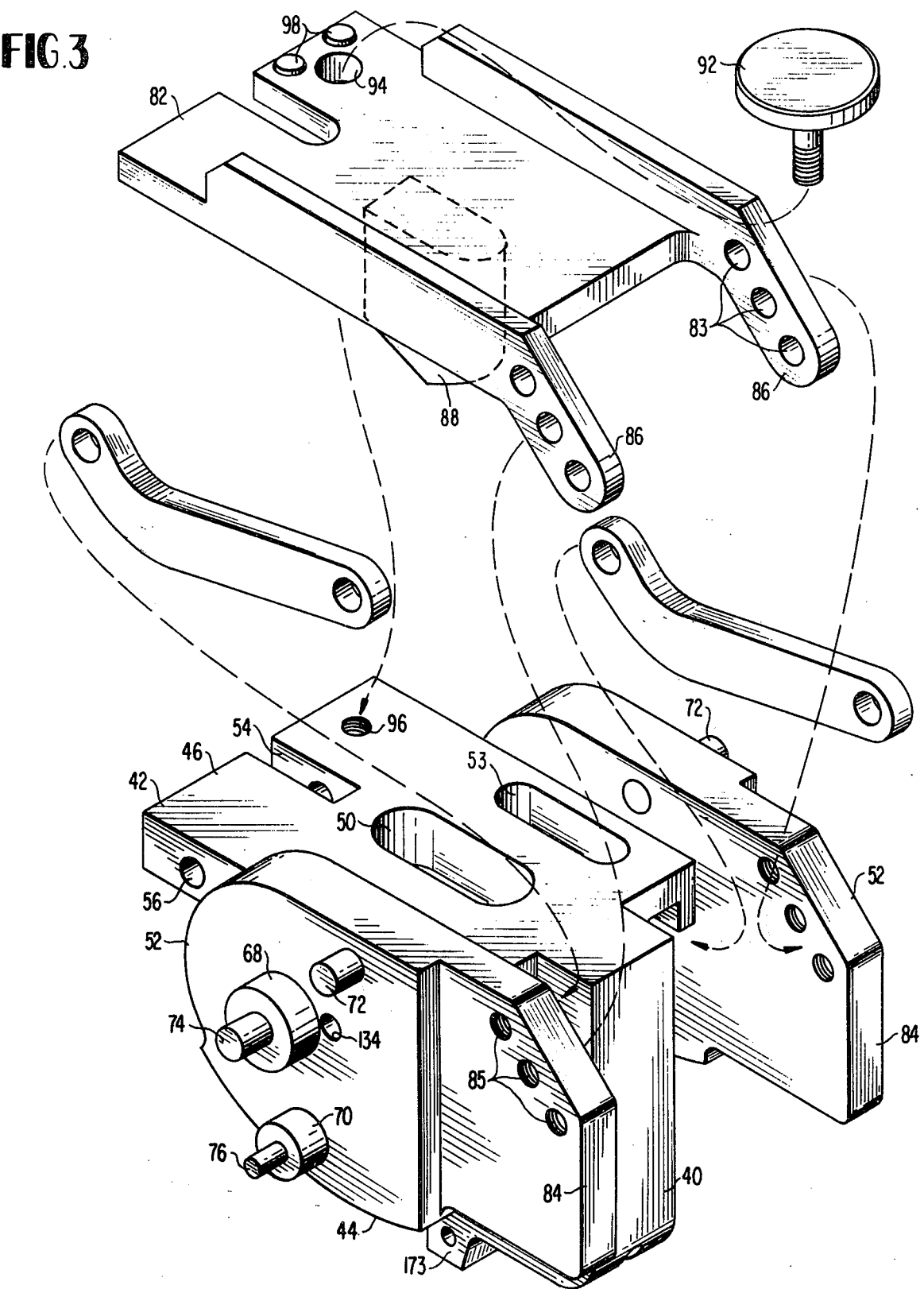

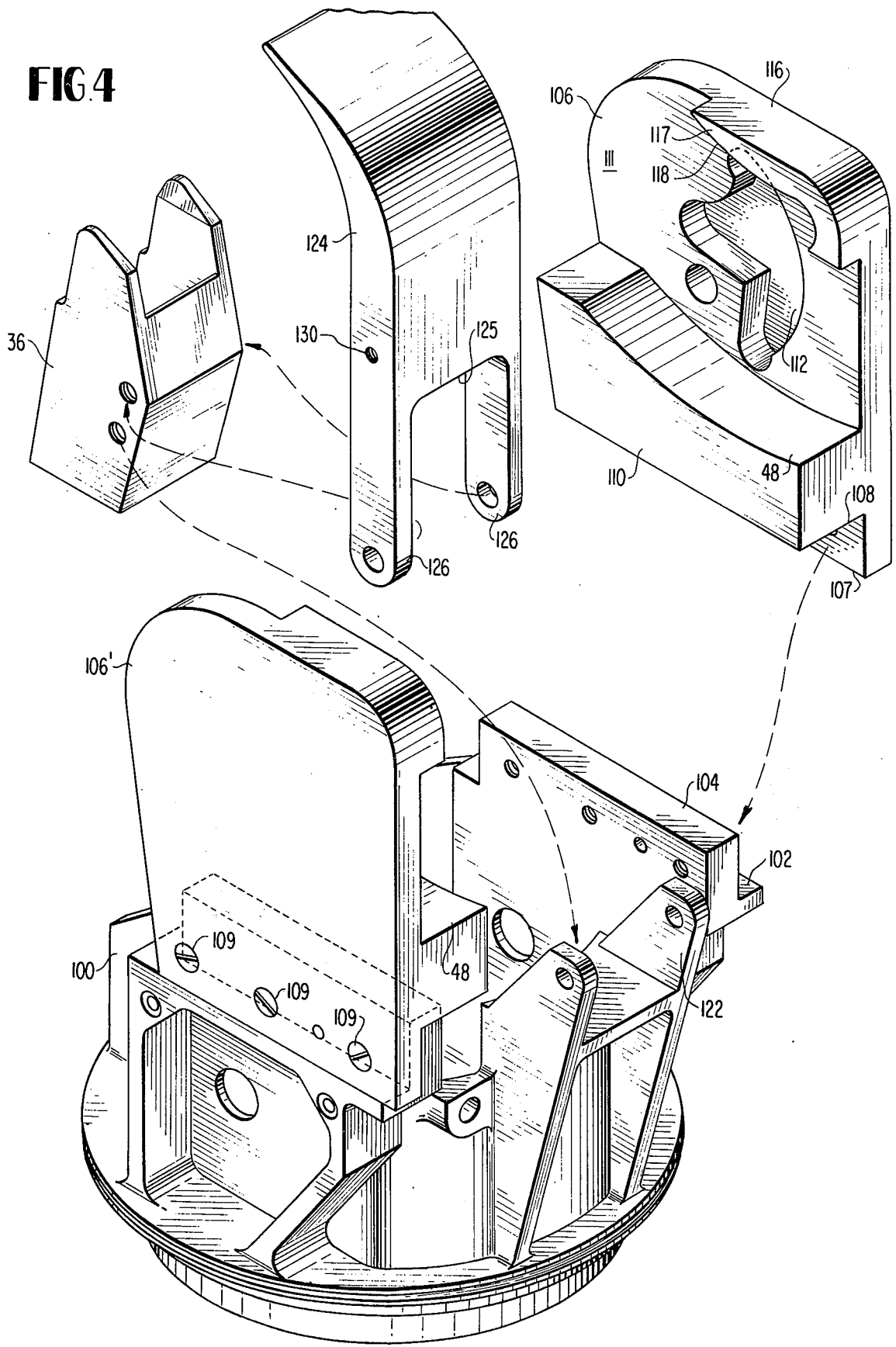

PROSTHETIC KNEE JOINT

CROSS REFERENCE TO RELATED APPLICATION

This application is a continuation-in-part of my copending application, Ser. No. 484,627, filed June 28, 1974, now abandoned, which is incorporated herein by this reference thereto.

BACKGROUND OF THE INVENTION

This invention relates generally to prosthetic knee joints for use by above-the-knee amputees. More particularly, this invention relates to prosthetic knee joints which simulate the motion of a natural knee.

In the past it has been common to employ simple pin joints in prosthetic knees. Simple pin joints, however, are inherently unstable in a standing posture unless the joint is provided with a stop means. Frequently, simple pin joints have a toggle action to provide a stop which gives the required stability. Such toggle actions, however, generally require an abnormally high force to cause initial flexion between femoral and tibial portions of a prosthetic leg. Moreover, simple pin joints result in a poor dynamic simulation of a human knee which has a very complex sliding and rolling motion between the femur and the tibia. Another problem with simple pin prosthetic knee joints is that they are difficult to brake effectively in a natural manner.

Another approach to the construction of a prosthetic knee joint has been the use of a polycentric joint. Typically such polycentric prosthetic knee joints comprise one or more links interconnecting a femoral member and a tibial member. The polycentric knee joints are generally quite complex. Moreover, the polycentric knee joints are also vulnerable to wear in addition to being noisy in use, even during simple ordinary walking. An additional disadvantage is that the multiple links are generally heavy and are susceptible to accidental damage.

A third construction for known prosthetic knee joints is the condylar knee joint. The condylar knee joints are characterized by articulable members which are provided condyles (i.e., articular prominences) that resemble the condyles of human femoral and tibial bones. Conventionally, the condylar surface of the femoral member and condylar surface of a tibial member are in contact such that there is constant rubbing friction therebetween during flexure between the femoral and tibial members. This constant friction presents an inherent disadvantage in such condylar knee joints: an amputee using the knee joint must continually exert energy to operate the knee joint unless there is some means of reducing the friction. Moreover, the friction between the tibial condyles and the femoral condyles results in a rapid wear of the rubbing surfaces. While lubrication may be used to eliminate the rapid wear, a messy knee joint results that is not well adapted to use in a prosthetic knee. Another disadvantage of conventional condylar knee joints is instability during a standing posture. Yet another disadvantage is that the condylar surfaces are frequently fabricated of materials which make the knee joint susceptible to accidental damage.

A common problem with previously known prosthetic knee joints is the inability to accommodate torsional motion between femoral and tibial portions of the joint which typically results during each step of normal walking and even more when one is following a curved path.

Recognizing the need for an improved prosthetic knee joint, it would therefore be desirable to provide a quiet, modular knee joint having a dynamic behavior, knee trajectory and load bearing capability which effectively simulates those characteristics in a natural knee joint.

In addition, it would be desirable to have a prosthetic knee joint which is not highly vulnerable to wear or accidental damage and which does not require lubrication.

An additional desirable feature for a prosthetic knee joint would be the provision of brake apparatus which resists the flexure of the knee joint with a force moment that increases with flexure of the knee joint and which provides shock absorbency for the prosthetic knee joint.

It would also be desirable to provide a prosthetic knee joint which will accommodate relative rotation between a natural hip joint and a foot such as that rotation which occurs when a normal individual is walking.

Another desirable feature of a prosthetic knee joint would be the incorporation of an extension aid which would facilitate the extension of the knee joint toward an unflexed position.

OBJECTS AND SUMMARY OF A PREFERRED EMBODIMENT OF THE INVENTION

It is therefore a general object of the present invention to provide a prosthetic knee joint of the condylar class which minimizes, reduces or eliminates problems of the type previously noted.

It is a more particular object of this invention to provide a novel prosthetic knee joint which will accommodate torsional movement within a prosthetic leg to which it is attached.

Another object of the invention is to provide a novel prosthetic knee joint in which load carrying surfaces roll relative to one another thereby substantially eliminating sliding friction, the wear associated therewith and the need for lubrication.

Yet another object of the invention is to provide a novel prosthetic knee joint having apparatus which cosmetically simulates the motion of the patella of a human knee.

Still another object of the invention is to provide a novel prosthetic knee joint having a weight actuated brake.

Yet still another object of the invention is to provide a novel prosthetic knee joint wherein a proportional brake generates a force moment which increases with the degree of flexure of the prosthetic knee joint.

A novel prosthetic knee joint according to a preferred embodiment of the invention intended to substantially accomplish the objects of this invention includes a femoral member having condylar bearing surfaces that are adapted for load-bearing rolling contact relative to differently contoured condylar bearing surfaces of a tibial member. Rollers, cam surfaces and slot surfaces of the tibial and femoral members cooperate to ensure rolling contact between the respective bearing surfaces. The knee joint also includes a brake that enables the femoral member and the tibial member to be frictionally retained in an articulated configuration. The tibial member is rotably mounted on a prosthetic lower leg to which one end of a torsion rod is connected. The other end of the torsion rod is connected to the knee joint to resiliently accommodate relative motion between the knee joint and the lower leg. The femoral and tibial members are connected to opposite ends of a dampening mechanism which aids in conforming the dynamic behavior of the prosthetic knee joint to the dynamic behavior of a natural knee.

BRIEF DESCRIPTION OF THE DRAWINGS

A preferred embodiment of the invention is illustrated in the accompanying drawings wherein:

FIG. 2 is a side elevation of the prosthetic knee joint in accordance with this invention;

FIG. 3 is an exploded isometric view of the femoral member with some parts removed for clarity;

FIG. 4 is a partially exploded isometric view of the tibial member;

DETAILED DESCRIPTION OF A PREFERRED EMBODIMENT OF THE INVENTION

In the following description of a preferred embodiment of the invention, certain terms are used with particular meaning as a matter of convenience. For example, "prosthetic knee joint" is used broadly to refer to a prosthetic knee joint per se in addition to the knee joint and the necessary connections with an upper prosthetic leg portion and a lower prosthetic leg portion. Similarly, "femoral" is used to refer broadly to the portion of the knee joint which would be connected with the thigh of an amputee using the prosthetic knee joint. In addition, "tibial" is used to refer to portions of the knee joint which would be connected to the prosthetic lower leg portion. "Patella" is used in reference to apparatus which simulates the motion of a patella or knee cap in a human leg.

"Anterior" refers to a direction generally on the right as shown in FIG. 2. Conversely, "posterior" refers to a direction generally to the left in FIG. 2.

Other words which are given a technical meaning are "flexion," "extension," and "hyperextension." "Flexion" refers to the articulation of a lower leg portion relative to an upper leg portion away from an aligned configuration. Conversely, "extension" refers to the articulation of a lower leg portion relative to an upper leg portion from a flexed position toward an aligned configuration therebetween. "Hyperextension" refers to the articulation of a lower leg portion relative to an upper leg portion away from an aligned configuration in an articulated direction opposite to that of flexion.

Figure 1:
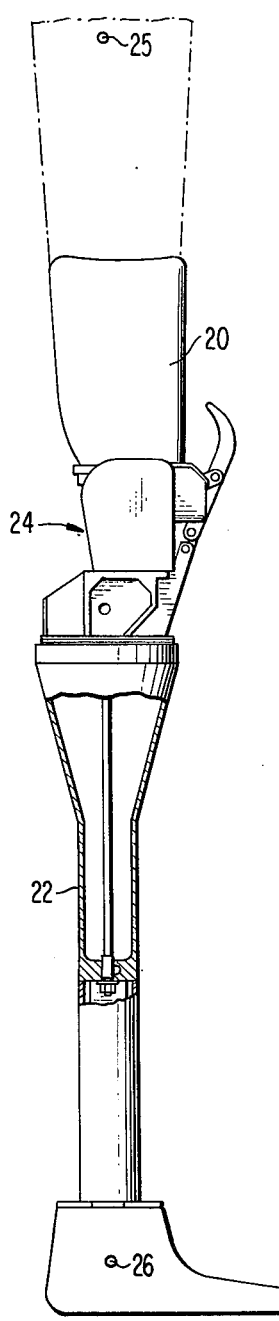
FIG. 1 is an elevation of a prosthetic leg incorporating the knee joint.

A prosthetic leg (see FIG. 1) comprises a femoral socket 20 that is articulatable relative to a tibial shank 22. The femoral socket 20 and the tibial shank are each connected to a knee joint 24 according to this invention.

The femoral socket 20 is connected to the thigh of an amputee for rotation about a femoral pivot point 25 which generally would be the amputee's hip joint and which is spaced above the knee joint 24. The tibial shank rotates about a tibial pivot point 26 which corresponds generally to an ankle and which is spaced below the knee joint 24.

It should be pointed out that the accompanying drawings display the mechanism devoid of cosmetic materials that restore the contour and feel of the prosthetic knee and adjoining areas to a good simulation of a normal knee and lower limb. Likewise cushioning and load bearing surfaces on the patella have not been shown. It is the intention of this invention that the shape, size, feel and load bearing portions should be individually sculptured by the attending prosthetist to the individual being fitted from oversized blocks of cushioning foam materials of the appropriate bulk properties which are attached and/or bonded on during manufacture. The joints and attachments of these generalized foam blocks being so arrayed to permit normal appearance in all joint positions. In many installations it will be advantageous to cover the finally shaped joint and lower limb with a stretched knit material such as cotton or nylon stockinet to achieve a smooth outer contour in all positions and to simulate the behavior of the normal skin covering.

The mechanism has been made small enough to permit this final sizing and shaping operation to be carried out optimally on all but about the smallest one percent of the adult men in the United States. Properly shaped and covered, the final knee and lower limb should appear through trousers to be a virtually perfect replica of the natural limb it is replacing. For women who may desire to wear dresses and snug fitting hosiery even more attention to appearance and restoration to normal coloration will be desirable.

Turning now to FIG. 2, the prosthetic knee joint comprises a femoral member or portion 30, a tibial member or portion 32, and a patella mechanism 34. The patella mechanism 34 simulates the motion of a patella or knee cap in a human leg when the femoral member 30 and the tibial member 32 are articulated. The patella mechanism 34 is quite important in a prosthetic knee joint both for cosmetic purposes and for permitting the amputee to kneel on hard and rough surfaces, without cutting his clothing or marking floors or surface coverings.

The femoral member 32 includes a femoral base 42 (see FIG. 3) and a pair of femoral bearing surfaces 44. Although only one femoral bearing surface 44 is illustrated in FIG. 3, both femoral bearing surfaces 44 are illustrated in cross section in FIG. 8. A pair of tibial bearing surfaces 48 are carried by a tibial base 100 as depicted in FIG. 4.

The weight of an amputee using a prosthetic knee joint according to this invention is transmitted from the femoral portion 30 (see FIG. 2) to the tibial portion 32 through the contacting arcuate femoral bearing surfaces 44 and the arcuate tibial bearing surfaces 48. The femoral and tibial bearing surfaces 44, 48 are designed to roll relative to each other as the femoral member 30 and the tibial member 32 are articulated.

The femoral base 42 (see FIG. 3) includes a generally planar top surface 46 which has a centrally located elongated opening 50. At each lateral side of femoral base is an integral cheek plate 52, each of which extends above the top surface 46 and which includes an arcuate femoral bearing surface 44 at the lower end.

Disposed between the central opening 50 and each cheek plate 52 is a link-receiving opening 52 which is elongate and is generally parallel to both the cheek plate 52 and the central opening 50. The posterior portion of the femoral base 42 is provided with a slot 54 that is in general alignment with the central opening 50, and like the central opening 50 and the link receiving openings 53, extends through the femoral base 42. A laterally extending bore 56 extends through the slot 54 from one side of the femoral base 42 and is adapted to receive a pin.

Figure 5:
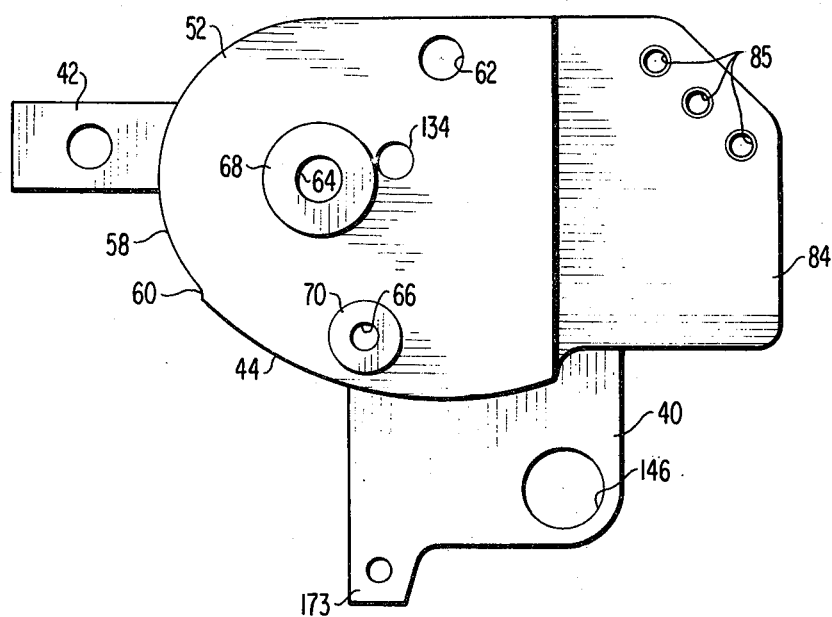
FIG. 5 is a side elevation of the femoral base of the prosthetic knee joint.
Figure 6:
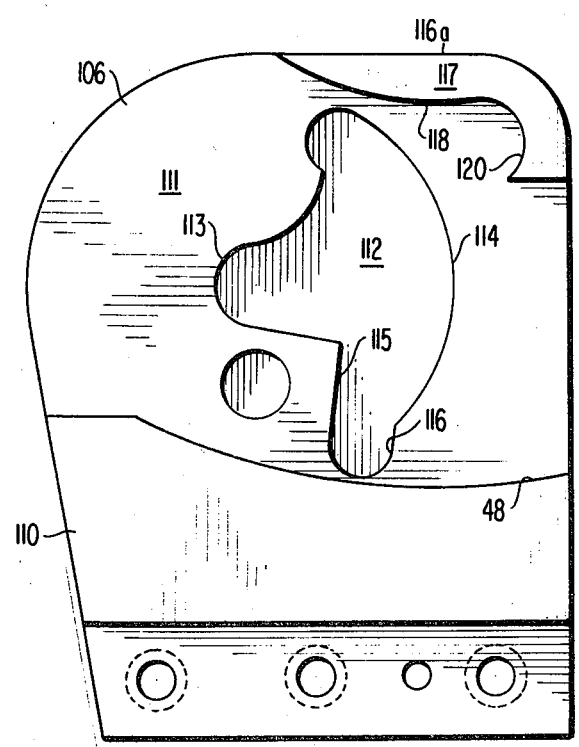
FIG. 6 is an elevation of the tibial bearing surface member.

Turning to FIG. 5, the arcuate configuration of the femoral bearing surface 44 is clearly illustrated. In addition the cheek plate 52 is seen to include a second arcuate surface 58 that is positioned posteriorly of the femoral bearing surface 44 and is located radially inwardly thereof at a shoulder 60.

Each cheek plate 52 includes a retainer pin bore 62 coaxially located at the center of curvature of the femoral bearing surface 44, and a pivot pin receiving bore 64 coaxially located at the center of curvature of the second arcuate surface 58. A guide pin receiving bore 66 is located in juxtaposition to the femoral bearing surface 44 and is positioned generally on the line bisecting the central angle subtended by the femoral bearing surface 44.

Each pivot pin receiving bore 64 and each guide pin receiving bore 66 are surrounded by an annular boss 68, 70, respectively, which extends laterally outwardly from the corresponding cheek plate 52. The annular bosses 68, 70 each extend a corresponding distance from the associated cheek plate 52 as may be seen from FIG. 3.

Each retainer pin bore 62 receives a retainer pin 72 which may be secured therein with an interference fit or in any other suitable manner. Similarly, each pivot pin receiving bore 64 receives a pivot pin 74 and each guide pin receiving bore 68 receives a guide pin 76. The pivot pins 74 and the guide pins may be secured with an interference fit or any other suitable manner.

Figure 8:
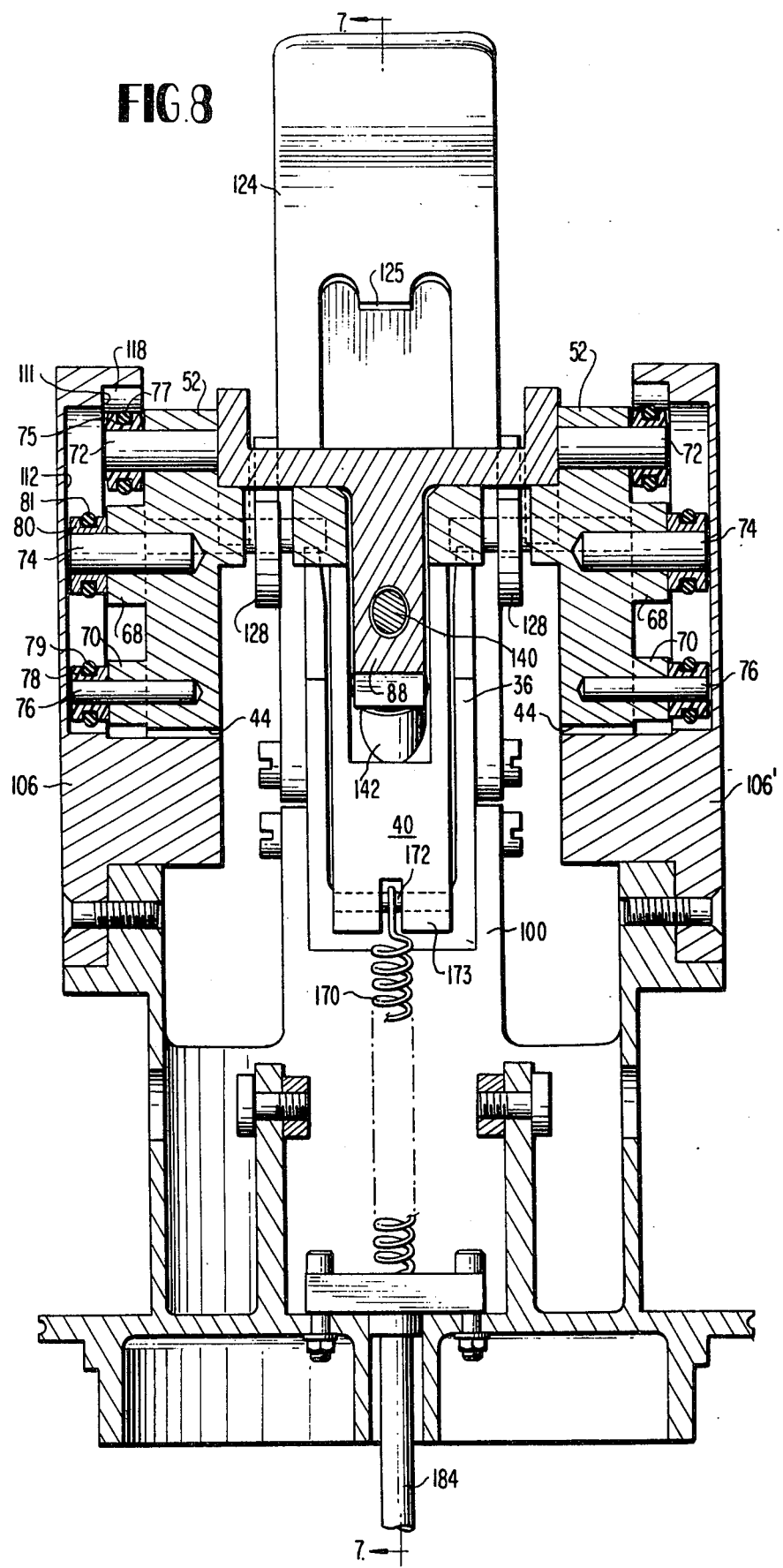
FIG. 8 is a cross-sectional view taken along line 8—8 of FIG. 2.

The retainer pin 72 extends from the cheek plate 52 such that the end thereof is roughly coplanar with the surfaces of the bosses 68, 70 (see FIG. 8). The pivot pins 74 and the guide pins 76 extend laterally from their corresponding bosses 68, 70 by a generally uniform distance.

A retaining roller 75 is rotatably mounted on each retaining pin 72. The retaining roller 75 preferably is fabricated from plastic material such as acetal resins manufactured under the trademark DELRIN and includes a circumferential groove that receives a suitably sized O-ring 77. The O-ring 77 is selected such that it projects beyond the cylindrical surface of the retaining roller 75.

The guide pin 76 is also provided with a rotatably mounted roller 78 having a circumferential groove that receives an O-ring 79. The roller 78 is preferably manufactured from plastic material such as acetal resins manufactured under the trademark DELRIN. In addition the O-ring 79 extends beyond the roller surface.

The pivot pin 74 preferably has a circumferentially grooved stainless steel roller 80 rotatably mounted thereon. As with the other rollers, an O-ring 81 is mounted in the circumferential groove and extends beyond the surface of the roller 80.

Disposed above the femoral base 42 (see FIG. 3) is a femoral plate 82 which includes a pair of anterior arms 86 that each include a plurality of holes 83. The femoral base 42 has anterior projections 84 each including a plurality of threaded holes 85. By aligning a pair of holes 83 with a pair of holes 85 and then inserting conventional threaded fasteners 87 (see FIG. 2) into the threaded holes, the femoral plate 82 may be pivotally secured to the femoral base 42. The femoral plate 82 is also provided with a centrally disposed projection 88 (see FIG. 7) which extends downwardly therefrom and is received in an opeing 90 of the femoral base 42.

Returning to FIG. 3, the femoral plate 82 includes a hole 94 through which a femoral plate upstop 92 passes to be received within threaded hole 96 of the femoral base 42. On the top surface of the femoral plate 82 a pair of resilient bumper pads 98 are provided which engage the under surface of the femoral pate upstop 92 and limit the pivotal motion of the femoral plate 82 relative to the femoral base 42.

Turning now to FIG. 4 the tibial member 32 comprises a tibial base 100 that is provided with a symmetrically disposed first pair of shoulders 102 and a symmetrically disposed second pair of shoulders 104. The first pair of shoulders 102 are positioned outwardly of the second pair of shoulders 104.

Mounted on each side of the tibial base 100 is a bearing plate 106, 106'. The two bearing plates 106, 106' are mirror images of one another and the description of one will suffice to likewise describe the pertinent features of the other. The lower edge 107 of each tibial bearing plate 106, 106' is provided with a rabbet 108. The lower edge 107 is supported by the shoulder 102 whereas the rabbet is supported by the shoulder 104 when the bearing plate 106 is assembled on the tibial base 100. Suitable threaded fasteners 109 may be used to attach each tibial bearing plate 106, 106' to the tibial base at a location between the shoulder 102 and the shoulder 104.

Each tibial bearing plate 106, 106' includes an arcuate tibial bearing surface 48 on the upper surface of a bearing projection 110. The tibial bearing surface 48 preferably has a radius of curvature which is twice the radius of curvature for the femoral bearing surface 44. With such a relationship between the arcuate bearing surfaces 44, 48, rolling contact therebetween is a hypocycloidal motion. Moreover, a point on the circumference of the femoral bearing 44 surface moves along a radial line of the tibial bearing surface 48.

The inwardly facing surface 111 of each tibial bearing surface 106, 106' is provided with a generally mushroom shaped slot or recess 112 which receives the pivot roller 80 (see FIG. 8) and the guide roller 78 carried by the femoral base 42. The recess 112 includes a socket portion 113 which has a radius slightly larger than the radius of the pivot roller 80. In addition the recess 112 includes an arcuate surface 114 facing the socket portion 113 and cam surfaces 115, 116 extending upwardly from the tibial bearing surface 48.

The cam surfaces 115, 116 are spaced apart by a distance slightly exceeding the diameter of the guide roller 78 and serve to constrain the movement of the guide roller 78 when the femoral base 42 moves relative to the tibial base 100 with hypocycloidal relationship. For manufacturing simplicity the cam surfaces may be parallel to a radius of the tibial bearing surface 48 without introducing substantial sliding during rolling movement of the femoral bearing surface 44 on the tibial bearing surface 48. The general absence of sliding is effected by the 2:1 relation between radii of the tibial and femoral bearing surfaces respectively in combination with the path of a point on the femoral bearing surface. The surfaces 115, 116 may, if desired, be given a contour which allows the guide roller to perfectly follow the trajectory it would have for purely rolling contact between the bearing surfaces 44, 48.

The arcuate surface 114 is spaced from the center of the socket portion 113 by a distance slightly exceeding the sum of the center-to-center distance between the pivot roller 80 and the guide roller 78 and the radius of the guide roller 78. In this manner, the guide roller 78 in cooperation with the arcuate surface 114 constrains the pivot roller 80 to the socket portion 113 during pivotal motion between the femoral base 42 and the tibial base 100.

At the upper edge 116a of each tibial bearing plate 106, 106' is a raised projection 117 having an arcuate surface 118 whose center is coincident with the center of the tibial bearing surface 48. The arcuate surface 118 is radially spaced from the tibial bearing surface 48 by a distance slightly greater than the sum of the radius of the femoral bearing surface 44 and the radius of the retaining roller 75. With the foregoing relationship, the retaining roller 75 cooperates with the arcuate cam surface 118 to avoid separation between the femoral member 42 and the tibial member 100 during hypocycloidal motion, to retain the guide roller 78 in engagement with the cam surfaces 115, 116 and to maintain contact between the femoral and tibial bearing surfaces 44, 48.

At the anterior end of the arcuate surface 118, an arcuate socket 120 is provided which cooperates with the retaining roller 75 to limit hyperextensive movement of the knee joint.

With reference to FIG. 4 the tibial base 100 is also provided at the anterior portion thereof with a generally U-shaped channel 122 in which one end of a steel brake shoe 36 is securely mounted by appropriate fastening devices.

Pivotally connected to the brake drum 36 are a pair of parallel fingers 126 each of which extend downwardly from a patella 124. The lower edge 125 of the patella between the fingers 126 comprises an abutment surface that is one part of a flexion limit stop. On each side of the patella 124, a bolt receiving opening 130 is provided for pivotal connection between the patella and one end of a generally J-shaped patella link 128 (see FIG. 7). The second end of each patella link 128 is pivotally connected to the femoral base 42 by a pivot pin 132 which is received in opening 134 (see FIG. 5) of the femoral base 42. The upper end of each link 128 is received in the corresponding link receiving opening 53 (see FIG. 3).

Figure 7:
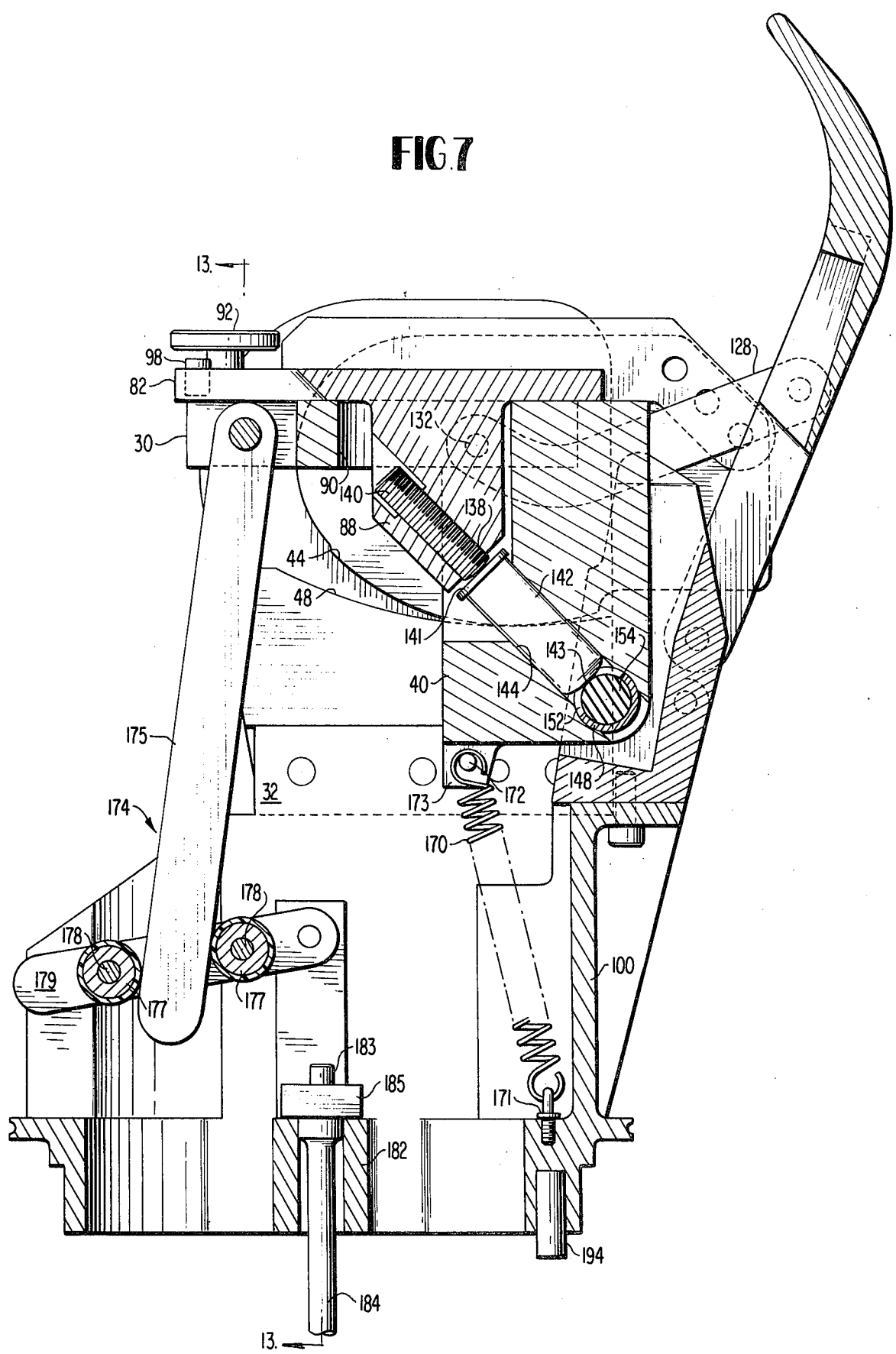
FIG. 7 is a cross-sectional view of the knee joint along the line 7—7 in FIG. 8.
Figure 9:
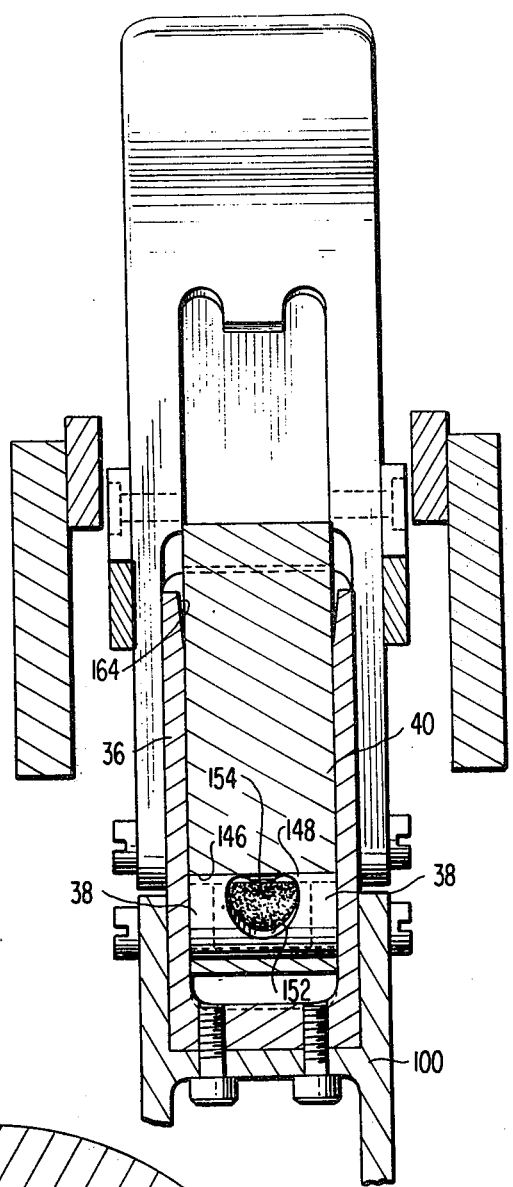
FIG. 9 is a cross-sectional view taken along line 9—9 of FIG. 2.

As best illustrated in FIG. 7, the projection 88 of the femoral plate 82 is provided with a bore 138 in which a threaded brake adjustment screw 140 is disposed. The femoral base 42 has a downwardly extending projection 40 which is provided with a bore 144. Slidably received in the bore 144 is a steel plunger 142 having a generally spherical end 143. The steel plunger 142 also includes a generally flat end 141 which is engaged by one end of the brake adjustment screw 140. The bore 144 intersects a transverse bore 146 in the projection 40 (see FIG. 9). Within the transverse bore 146 a cylindrical shell 148 is coaxially disposed and securely positioned such as by a set screw (not shown). The cylindrical shell 148 is oriented in the transverse bore 146 such that an opening 152 in the cylindrical surface thereof is maintained in alignment with the spherical end 143 (see FIG. 7) of the steel plunger 142. Disposed within the cylindrical shell 148 is a cylindrical resilient deformable element 154 which has a disc-shaped brake shoe 38 securely bonded to each end thereof (see FIG. 9). Preferably, the brake shoes 32 are fabricated from conventional automotive disc brake material. The element 154 is preferably formed of an elastomeric material such as silicone rubber which provides automatic retraction of the brake shoes 38 and which comprises a volumetric resolver for displacement generated by the protrusion of spherical end 143 into the element 154.

The actuation of the brake shoes 38 will now be described in connection with FIG. 7. To apply force to the brake shoes 38, a force is applied to the pivotally mounted femoral plate 82. The force applied thereto may result from a shift of weight by an amputee to a prosthetic leg which incorporates the knee joint or by a rearward force applied through the remaining part of the amputee's thigh (commonly called his stump). The applied force causes the femoral plate 82 to rotate counterclockwise about the pivotal connection between arms 86 thereof and femoral base 42 thereby causing the brake adjustment screw 140 to bear against the flat end 141 of the plunger 142. The plunger 142 is thus translated within the bore 144 such that the spherical end 143 intrudes through the opening 152 to displace a portion of the resilient element 154 (see FIG. 9). The displacement of the member 154 occurs centrally thereof and generates an internal pressure which causes the two ends of the member 154 and the brake shoes 38 bonded thereto to be expressed axially of the transverse bore 146. The brake shoes 38 engage the opposed internal surfaces of the brake drum 36 which is secured to the tibial base 100.

Rubbing of the brake shoe 38 on the drum provides a friction coefficient which is relatively high and well suited for a prosthetic knee joint brake application. In addition, the easily replaceable inexpensive brake shoes 38 constitute the primary wearing surface of the brake mechanism. By providing the brake shoes 38 at opposite ends of the resilient member 154, the brake mechanism is self balancing and will not create any unbalanced forces or moments.

When the force applied to the femoral plate 82 is released, the resilient element 154 will, as noted, elastically disengage the brake shoes 38 from the brake drum 36. While the knee joint is in use by an amputee, any movement by him which will cause an extension moment will thus automatically release the brake mechanism.

Another feature of the brake mechanism is an inherent shock absorbancy by which the resilient member 154 compensates for impulsive forces which would tend to cause further flexion of femoral and tibial members 30, 32.

The primary adjustments for the brake mechanism are illustrated in FIG. 7. The first adjustment is the threaded screw 140 carried by the central projection 88 of the femoral plate 82. By adjusting screw 140, the residual force exerted on the brake shoes 38 may be controlled. Moreover, screw 140 may be used to compensate for wear of the shoes 38. The femoral upstop 92, described above, provides a second adjustment whereby the vertical travel of the femoral plate 82 may be varied. The femoral upstop 92 in combination with the adjusting screw 140 makes possible control of the amount of relative rotary movement of femoral plate 82 with respect to the femoral base 42 to fully set the brake shoes 38 in engagement with the brake drum 36 surfaces.

It will also be noted from FIG. 7 that the resilient bumper pads 98 carried by the femoral plate 82 eliminate metal to metal contact between the femoral upstop 92 and the femoral plate 82 thereby eliminating one source of noise.

As noted, each roller 75, 78, 80 is provided with a corresponding O-ring 77, 79, 81. The O-rings provide a resilient spacing between the associated roller and the cooperating surfaces thereby eliminating metal-to-metal contact, reducing noise and adding some shock absorbency.

With reference to FIG. 7, an extension spring 170 is provided to facilitate extensional movement between the femoral member 30 and the tibial member 32. One end of each spring 170 is suitably secured to the tibial base 100 at an internal anterior position 171. The other end is suitably secured to the femoral base 42 such as by a pin 172 extending between downwardly extending projection 173. The projections 173 comprise a second portion of the flexion limit stop which cooperates with the abutment surface 125. Tension in the spring is adjusted to regulate the swing phase of walking. The tension must take into account the total active weight of the prosthetic limb, shoes, and clothing which is suspended from the femoral member 30. The tension must also provide additional force to compensate for forces dynamically introduced in normal walking.

Figure 13:
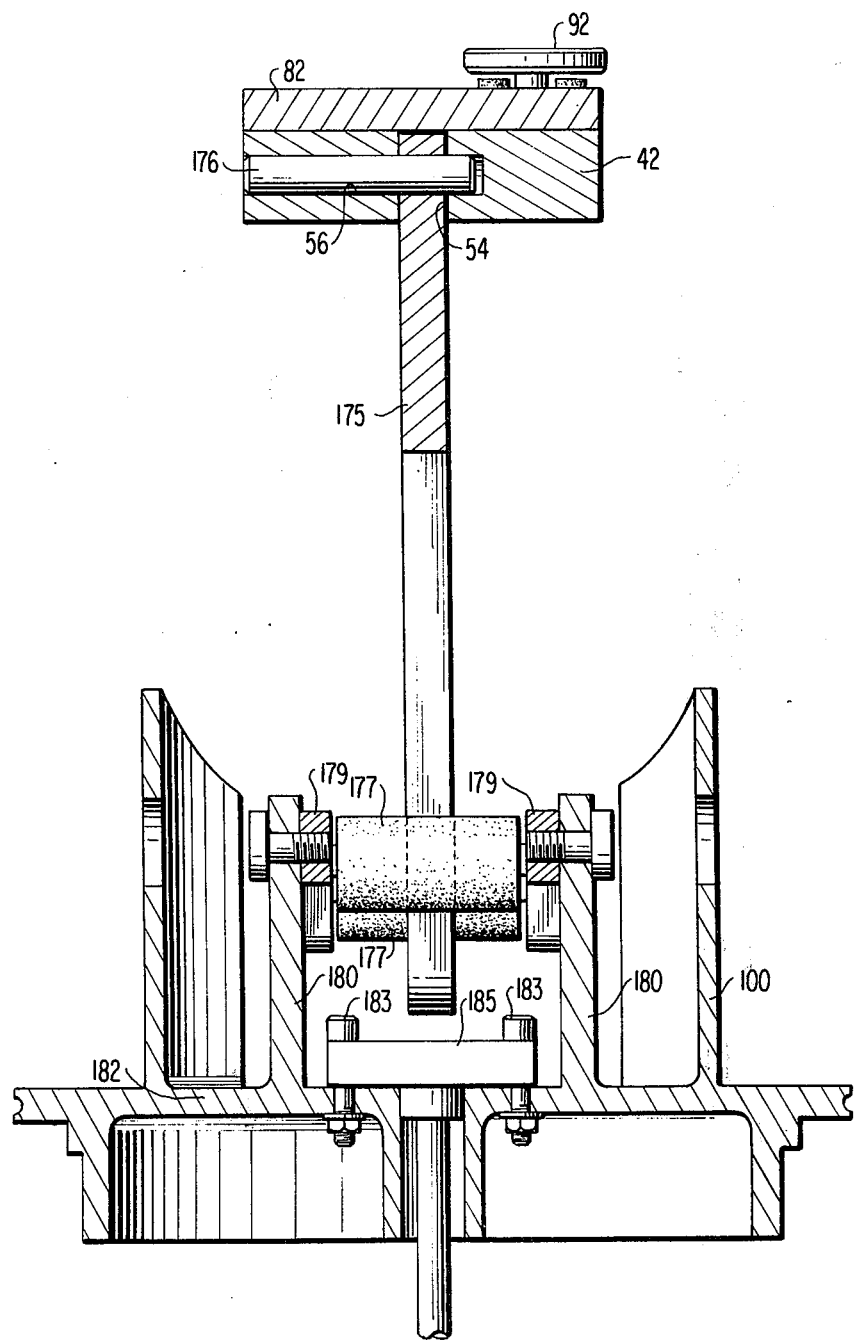
FIG. 13 is a cross-sectional view taken along line 13—13 of FIG. 7.

A dampening mechanism 174 (see FIG. 7) may be provided in the knee joint for better simulation of the dynamic movement of a natural knee. A particularly suitable dampening mechanism may be constructed in accordance with my copending U.S. patent application entitled "Motion Damper," executed May 27, 1975, filed June 20, 1975, Ser. No. 588,626, now U.S. Pat. No. 3,960,247, and assigned to the assignee hereof. My entire "Motion Damper" application is incorporated herein by this reference thereto. The dampening mechanism 174 includes an actuator bar 175 having an opening in one end portion to receive a pivot pin 176 (see FIG. 13) that is received within the bore 56 of the femoral base. The end portion of the actuator bar 175 is received in the slot 54 and is thus pivotally connected to the femoral base 42.

The lower end portion of the actuator bar 175 extends between and beyond a pair of spaced apart resiliently covered rollers 177. Each roller 177 is rotatably mounted on a shaft 178 which, in turn, is mounted on a pair of spaced apart fixed links 179. Each link 179 is secured to the posterior portion of the tibial base 100 and to a corresponding upright mounting bracket 180 that extends upwardly from a cross-member 182 positioned centrally in the tibial base 100.

As the femoral member 30 and the tibial member 32 move relative to one another, the friction resistance to movement of the actuator bar 175 varies by virtue of the compressive force acting on the bar 175 by the resilient covering on the rollers 177. Accordingly, the frictional drag on the actuator bar 175 can be varied by changing the cross-sectional dimensions of the actuator bar 175, the spacing of the rollers 177 and the inclination of the links 179 relative to the tibial base 100.

A torsion rod 184 having a generally circular cross section and a bar 185 attached to one end is preferably rigidly attached to the cross member 182 by means of two bolts 183. The second end of the torsion rod 184 may be provided with a flat or with a D-shaped cross-section. The second end is connected to the tibial shank 22 (see FIG. 1) so that there is no relative motion therebetween.

Torsional motion between the hip joint 25 and the ankle 26 may be accommodated by placing a bearing 187 between the lower end of the tibial base 100 and the upper end of the tibial shank 22 (see FIG. 2). The tibial shank 22 is mounted on the lower race 186 of the ball bearing 187. The upper race 188 of the ball bearing 187 is mounted on the tibial base 100. Grease is provided between the upper and lower races 188, 186 to dampen torsional motion. To prevent escape of grease from the bearing 186, seal rings 189, 190 are disposed between the upper and lower races 186, 188. Preferably the seal rings are fabricated of beryllium copper alloy. The seal is important for 3 reasons:

1. to keep the grease intact for its dampening function;
2. to keep foreign matter out of the bearing; and
3. to keep grease from soiling clothes.

Sliding friction is kept at low as possible so that the torsion rod can unambiguously recenter the foot whenever the limb is unweighted.

Figure 10:
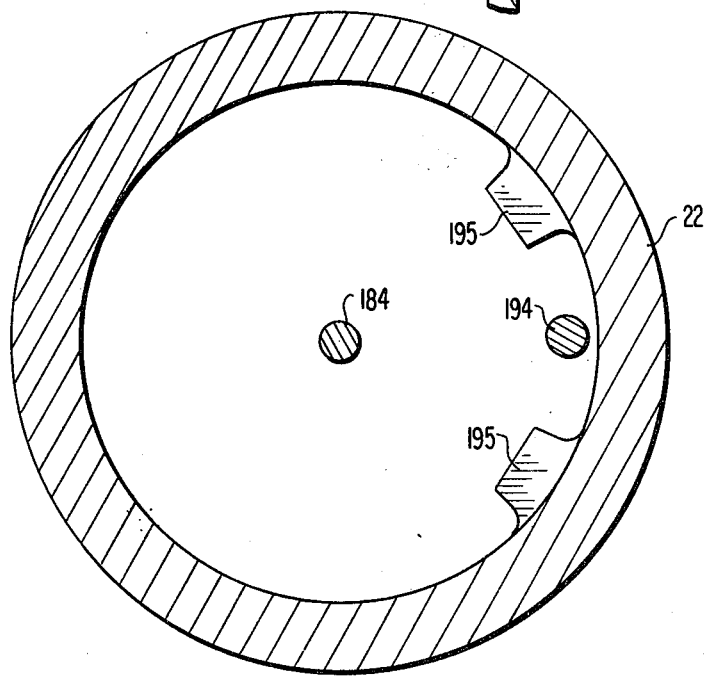
FIG. 10 is a cross-sectional view taken along line 10—10 of FIG. 2.

The tibial base 100 includes a pin 194 (see FIG. 2) which extends downwardly from the bottom surface thereof. The pin 194 engages radially inwardly projecting pin stops 195 of the tibial shank 22 (see FIG. 10) which limit torsional ovement between the tibial shank 22 and the knee joint 24. The allowable range of movement provided is approximately equivalent to the rotation followed in a normal knee and ankle and is safely below the yield characteristics of the torsion rod 184.

Figure 11:
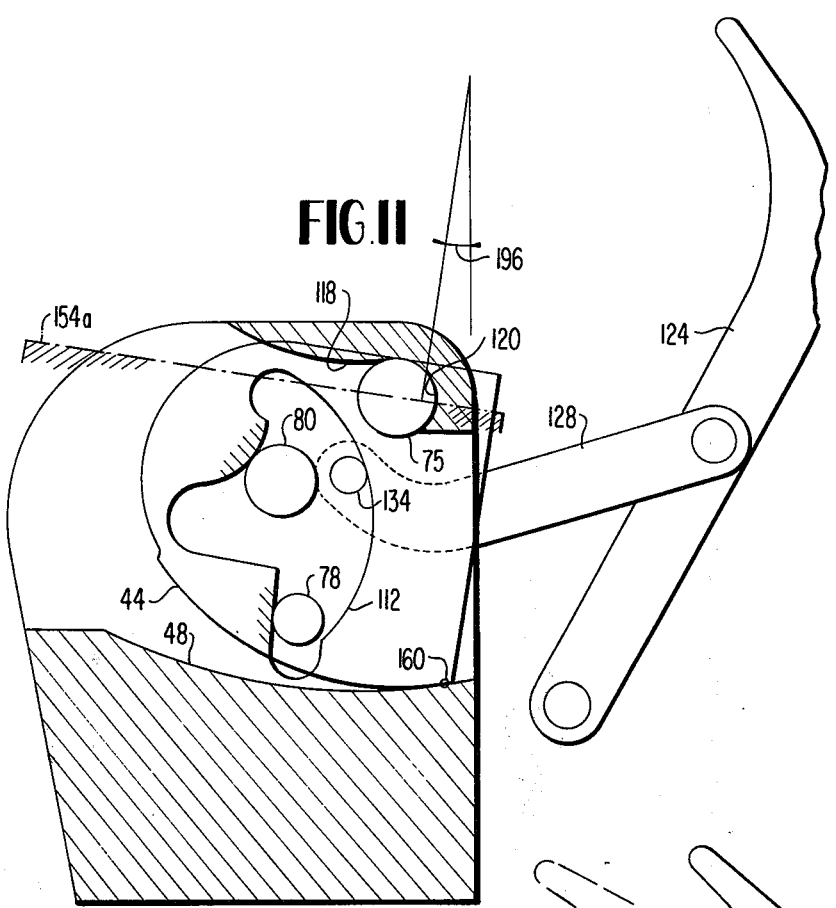
FIG. 11 is a schematic view of selected parts of the knee joint at the limiting hyperextended position.
Figure 12:
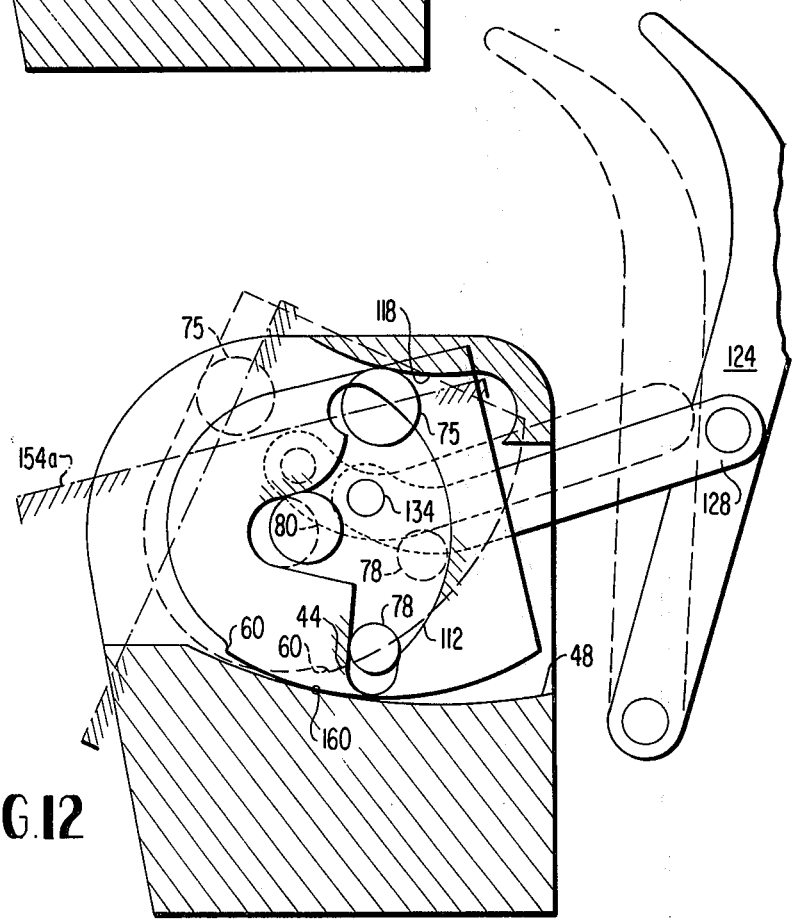
FIG. 12 is a schematic view of selected parts of the knee joint at progressively increasing flexed positions.

To assist an understanding of the operation of the prosthetic knee joint of this invention, FIGS. 11 and 12 schematically illustrate the position of the tibial bearing surface 48 and the femoral bearing surface 44 for various angles of articulation of a prosthetic leg which incorporates the prosthetic knee joint of this invention. To help visualize the attitude of the tibial member 32 relative to the femoral member 30, a femoral reference plane 154a is illustrated in FIGS. 11 and 12 and comprises a surface parallel to the femoral base 42. In addition, FIGS. 11 and 12 illustrate the movement of the patella 124 and the patellar links 128 for different articulated positions of the prosthetic knee joint. These figures also illustrate the movement and positioning of the rollers 75, 78, 80 carried by the femoral base 42 with respect to the slot 112 of the tibial bearing plate 106.

Depicted in FIG. 11 is the maximum hyperextended configuration from which it will be noted that retaining roller 75 is engaged within the anterior arcuate portion 120 of slot 112 thereby providing a mechanical stop which prevents the prosthetic knee joint from uncontrolled unlimited hyperextensive movement.

The broken lines of FIG. 2 illustrate the configuration of the parts illustrated in FIGS. 11 and 12 when the prosthetic knee joint is in an unflexed or standing configuration.

As the prosthetic knee joint is flexed from the straight configuration illustrated in FIG. 2, the femoral bearing surface 44 and the tibial bearing surface 48 have rolling contact with each other. It will be seen from a comparison of FIGS. 2 and 11 that a contact axis 160, which is defined by the point of contact between the bearing surfaces 44, 48, progresses in a posterior direction as the prosthetic knee joint is flexed. The rollers 75, 78 discussed above do not transmit any load bearing force but are provided to insure that the rolling contact between the tibial bearing surface 48 and the femoral bearing surface 44 occurs and that shear loading induced by the brake does not induce slippage. The pivot rollers 80 need not be in contact with the surfaces of recess 112 as illustrated by FIG. 11. The surfaces of recess 112 comprise cam surfaces with which the rollers 78, 80 must cooperate. The primary function of the retaining roller 75 and the cooperating cam surface 118 is to prevent disengagement of the femoral bearing surface 44 and the tibial bearing surface 48 in the event that large forces tending to pull the joint apart are experienced.

It is useful to define an articulation angle (see FIG. 11) as the acute angle 196 between a first line normal to the upper surface of the femoral member 30 and a second line normal to the lower surface of the tibial member 32.

An examination of FIGS. 2, 11 and 12 illustrates the movement of the schematically illustrated parts during flexure of the prosthetic knee joint through progressively increasing articulation angles. It will be noted that the contact axis 160 moves progressively rearward and the pivot roller 80 moves toward the socket portion of the recess 112. Between the 7 ½° articulation angle of hyperextension and about a 22 ½° articulation angle of flexion, the femoral member 30 and the tibial member 32 move in a generally hypocycloidal relationship. During this hypocycloidal movement, the femoral pivot 134 of the patella link 128 moves posteriorly causing the patella 124 to pivot in a posterior direction. When the pivot roller 80 is seated in its socket (see FIG. 12), the motion between the femoral member 30 and the tibial member 32 resembles that of a simple hinge joint. To prevent an accidental dislocation of the pivot roller 80 from the socket, the guide roller 78 engages the arcuate cam surface of the recess 112. When the contact axis 160 has moved rearwardly and coincides with the shoulder 60, the transition from hypocycloidal to pivotal motion occurs. In this connection it will be observed that the shoulder 60 allows a radial clearance to be effected so that there is no sliding friction between the femoral and tibial bearing surfaces during subsequent articulation. The continued flexing of the prosthetic knee joint is mechanically limited by the engagement of the projections 173 of the femoral base (see FIG. 3) with the abutment edge 125 of the patella 124 as it pivots rearwardly. The limiting articulation angle is selected at about 130°. The recess 112 is so designed that the guide roller 78 does not bottom out at the upper end of the recess 112 before the flexion limit is reached. This eliminates the need for a massively sized guide roller shaft to accommodate the high force moments encountered at the flexion limit.

A brake force moment results from the frictional force applied by the brake shoes acting at a distance from the contact axis 160 about which the femoral and tibial members articulate. Having described above the manner whereby the contact axis 160 moves progressively posteriorly as the articulation angle increases, it should be apparent that the anterior position of the brake drum 36 and brake shoes 38 makes possible a brake force moment whose magnitude increases with the angle of articulation thus comprising a proportional brake mechanism in which the effectiveness of the applied force to support the amputee's weight may be kept essentially constant in spite of changes in knee flexion.

From FIG. 7 it may be observed that the brake shoes 38 carried by the anterior projection 40 of the femoral base 42 will engage the U-shaped channel of brake drum 36 only during a portion of the allowable 130° articulation. The actual range of porportional braking is up to an articulation angle of approximately 45°. To ensure that the brake shoes 38 properly reposition themselves in the brake drum 36 during extensional movement, the brake drum is provided with slightly inclined surfaces 164 at the top of each internal surface contacted by a brake shoe 38 (see FIG. 9).

In normal walking articulation angles of 0°–70° are encountered. Articulation angles of 100°–130° occur primarily in kneeling and stooping postures. As a result of habits of human beings, the articulation angles exceeding 90° are infrequently encountered. Accordingly, in designing a prosthetic knee joint, the primary emphasis for natural dynamic and visual characteristics can be limited to the articulation angles from 0° to 90°.

The bearing surfaces 44, 48 cooperate to exhibit several of the desired dynamic characteristics for a knee joint. Accordingly, a first predetermined articulation angle (approximately 0°) corresponds to the position of the femoral member 30 and the tibial member 32 in a standing posture. The points on the bearing surfaces 44, 48 used in defining the articulation angle correspond to the position of the contact axis 160 during standing. At this first angle, the distance between femoral pivot point 25 and tibial pivot point 26 comprises a relative minimum.

For articulation angles greater than or less than the first angle but lower than a second predetermined articulation angle (approximately 22 ½°) the distance exceeds the relative minimum. The first range of articulation angles encompasses both flexion and hyperextension. Where the articulation angle corresponds to the second angle, the distance is a relative maximum.

At articulation angles greater than the second angle the distance is less the relative maximum and stability is determined by the hip and foot position and the knee joint functions as a simple pivot.

A prosthetic knee joint incorporating the arcuate bearing surfaces 44, 48, as disclosed here, has the desirable characteristic of generating a self-righting moment which tends to decrease the articulation angle. The self-righting moment is generated in the first range of articulation angles by the fact that lower articulation angles bring the amputee's hip joint closer to a prosthetic ankle joint. Physically, the convex portion of the femoral bearing surface which is supported by the tibial bearing surface enhance the generation of the self-righting moment. The self-righting moment provides an inherent stability for the knee joint which requires only a conscious effort to overcome. Moreover, due to the self-righting moment, the proportional brake mechanism is an additional feature which is not absolutely essential to the proper functioning of a knee joint according to this invention.

Having described the knee joint and its features, the manner in which a prosthetic leg incorporating it is used by an amputee can now be understood. As the heel of the essentially straight leg strikes a supporting surface, the amputee begins to apply body weight to the leg and simultaneously introduces a small amount of flexion. This action may be quickly learned and relegated to subconscious habit patterns and simulates virtually perfectly the way a normal person walks presumably to minimize the vaulting effect which would otherwise be present in a stance phase of walking.

The weight sets the proportional brake thus braking the leg against additional flexing. As the leg pivots forwardly about the heel at the completion of the stance phase, extensional movement of the knee joint occurs thus straightening the leg again in a naturally appearing manner which requires no conscious thought or additional movements or forces.

The amputee's natural leg has then been placed ahead of him in flexed weight-receiving position. The amputee then begins shifting weight from the prosthetic leg to the natural leg. The prosthetic leg is then flexed by moving the thigh portion forwardly while inertia of the lower leg portion continues the flexing movement.

The extension spring 170 helps to overcome the flexing movement accompanying heel rise and to then generate extensional moments in the leg thus assisting its inherent momentum and aiding it is extending and in swinging it forward. This action permits storage and reuse of energy and minimize the energy consumed in walking. The extensional movement is dampened to provide a naturally appearing deceleration so that the leg will not stop abruptly with attendant high forces being transmitted to the stump. The dampening also reduces noise and the possibility of rebound against the positive stops. The leg will then smoothly assume the straight orientation just prior to the time the heel is again ready to strike the supporting surface.

While the femoral rollers 75, 78, 80, the tibial bearing plates 106, 106', and the bearing surfaces 44, 48 are illustrated in the drawings as being symmetrical, it would be a relatively simple modification to give slightly different surface contours to the gears and bearing surfaces on each side of the knee joint to accommodate the small amount of torsional motion which occurs between the femur and tibia of a natural leg during natural walking. The corresponding motion in a natural knee joint is referred to as abduction-adduction.

The foregoing detailed description of a preferred embodiment of the invention is not intended to comprise a limitation on the scope of the appended claims. Many modifications, alterations, substitutions, and equivalents for features of this invention as defined by the claims may appear to those skilled in the art. Accordingly, any and all modifications, alterations, substitutions, and equivalents for features of this invention as defined by the claims are expressly intended to be encompassed thereby.

What is claimed is:

1. A prosthetic knee joint for an artificial leg comprising:
    a tibial member having at least one tibial bearing surface, said at least one tibial bearing surface having a first arcuate configuration,
    a femoral member being movable relative to said tibial member and having at least one femoral bearing surface, said at least one tibial bearing surface having a second arcuate configuration supportingly engaging said at least one femoral bearing surface;
    rolling contact means for establishing rolling contact between said at least one femoral bearing surface and said at least one tibial bearing surface substantially along the entire length of said tibial bearing surface while preventing substantial sliding movement between said tibial bearing surface and said femoral bearing surface; and
    engagement means for preventing disengagement of said at least one femoral bearing surface and said at least one tibial surface during rolling movement therebetween.

2. The prosthetic knee joint of claim 1 wherein said tibial bearing surface is concave and wherein said femoral bearing surface is convex.

3. The prosthetic knee joint of claim 2 wherein the radius of curvature of the tibial bearing surface is twice the radius of curvature of the femoral bearing surface.

4. The prosthetic knee joint of claim 1 wherein said rolling contact means includes:
    guiding roller means for positioning said femoral bearing surface and said tibial bearing surface relative to one another, said guiding roller means projecting laterally from said femoral member; and
    slot means on said tibial member for receiving said guiding roller means, said slot means having cam surfaces against which said guiding roller means is guided such that said guiding roller means and said slot means cooperate to substantially eliminate sliding motion between said femoral bearing surface and said tibial bearing surface.

5. The prosthetic knee joint of claim 1 wherein said engagement means includes:
    retaining roller means for inhibiting separation of said femoral and tibial bearing surfaces, said retaining roller means projecting laterally from said femoral member; and
    cam surface means for cooperating with said retaining roller means to inhibit bearing surface separation, said cam surface means carried by said tibial member and having a contour configured to constrain the retaining roller means to the trajectory defined by rolling contact between the bearing surfaces.

6. The prosthetic knee joint of claim 4 including:
    pivot roller means for permitting simple pivotal motion between said femoral member and said tibial member, said pivot roller means projects laterally from said femoral member and moves freely within said slot means during rolling motion between said femoral and tibial bearing surfaces;
    said slot means includes a socket for receiving said pivot roller means at the posterior end of said rolling motion and an arcuate surface for constraining movement of said guiding roller to a circular arc throughout said pivotal motion; and
    said guiding roller means cooperating with said arcuate surface to retain said pivot roller in said socket.

7. In a prosthetic knee joint having a femoral member and a tibial member mounted for relative movement wherein the improvement comprises:
    means for simulating a patella, said means for simulating pivotally connected to said femoral member and pivotally connected to said tibial member and said means for simulating a patella includes at least one patellar member pivotally connected to said tibial member, and at least one patellar link having one end pivotally connected to said femoral member and another end pivotally connected to said patellar member, whereby said at least one patellar member moves in response to relative movement between said femoral member and said tibial member.

8. In a prosthetic knee joint having a femoral member and a tibial member mounted for relative movement wherein the improvement comprises:

means for simulating a patella, said means for simulating pivotally connected to said femoral member and pivotally connected to said tibial member;

at least one patellar member pivotally connected to said tibial member;

at least one patellar link having one end pivotally connected to said femoral member and another end pivotally connected to said patellar member, whereby said at least one patellar member moves in response to relative movement between said femoral member and said tibial member;

wherein said at least one patellar member is pivotally connected to an anterior portion of said tibial member; and wherein said at least one patellar link is pivotally connected to a posterior portion of said femoral member.

9. A prosthetic knee joint having a pair of relatively movable members wherein the improvement comprises:

a brake drum provided for one of said pair of members and having opposed braking surfaces;

resilient brake shoe means carried by the second of said pair of members and having a longitudinal member with spaced ends positioned adjacent the braking surfaces, the longitudinal member being operable to increase spacing between said ends in response to a transverse squeezing force so that the resilient brake shoe means is operable to frictionally engage said brake drum;

means for selectively applying a transverse squeezing force to said longitudinal member, said means for applying force carried by the second of said pair of members, whereby said resilient brake shoe means engages said brake drum to resist relative movement between said pair of relatively movable members.

10. The knee joint of claim 9 wherein:

said longitudinal member is a deformable resilient element having at least one brake shoe connected to at least one end of said deformable resilient element; and wherein said means for selectively applying force selectively engages said deformable resilient element which transmits a related force to said at least one brake shoe.

11. The knee joint of claim 10 wherein:

said force applying means includes a lever pivotally mounted on the second of said pair of members and a plunger having two ends, one end being operatively connected to said lever and the second end engaging said deformable resilient element.

12. A prosthetic knee joint having a pair of relatively movable members wherein the improvement comprises:

a brake drum provided for one of said pair of members;

brake shoe means for frictionally engaging said brake drum, said brake shoe means carried by the second of said pair of members;

means for selectively applying force to said brake shoe means, said means for applying force carried by the second of said pair of members;

whereby said brake shoe means engages said brake drum to resist relative movement between said pair of relatively movable members;

wherein said brake shoe means includes a deformable resilient element having at least one end and having at least one brake shoe connected to said at least one end of said deformable resilient element;

wherein said means for selectively applying force selectively engages said deformable resilient element which transmits an applied force to said at least one brake shoe;

said at least one brake shoe fabricated from brake shoe material; and said deformable resilient element disposed within a cylindrical member having an opening in the cylindrical surface thereof to receive said plunger.

13. A proportional brake for a prosthetic knee joint comprising:

a prosthetic knee joint which includes a pair of relatively movable members that contact one another at a pivot axis, said pivot axis moving posteriorly of said knee joint when said knee joint is flexed and moving anteriorly of said knee joint when said knee joint is extended;

brake means for resisting flexure of said knee joint, said brake means connected to said knee joint anteriorly thereof; and means for selectively operating said brake means, said means for selectively operating being carried by one of said pair of relatively movable members, whereby a force moment tending to flex said prosthetic knee joint is resisted by a braking force moment which increases with flexure of said knee joint due to posterior movement of said pivot axis away from said anteriorly positioned brake means.

14. The proportional brake of claim 13 wherein said brake means includes:

a brake drum provided anteriorly of one of said pair of relatively movable members;

brake shoe means for frictionally engaging said brake drum, said brake shoe means anteriorly carried by the second of said pair of relatively movable members; and means for selectively applying force to said brake shoe means, said means for applying force carried by the second of said pair of relatively movable members.

15. The proportional brake of claim 14:

wherein said brake shoe means includes a deformable resilient element having at least one end and having at least one brake shoe connected to said at least one end of said deformable resilient element; and wherein said means for selectively applying force selectively engages said deformable resilient element which transmits an applied force to said at least one brake shoe.

16. The proportional brake of claim 15:

wherein said force applying means includes a lever pivotally mounted on the second of said pair of members and a plunger having two ends, one end being operatively connected to said lever and the second end engaging said deformable resilient element.

17. A proportional brake of claim 16 including:
said at least one brake shoe being fabricated from brake shoe material; and
said deformable resilient element being disposed within a cylindrical member having an opening in the cylindrical surface thereof to receive said plunger.

18. A prosthetic knee joint for an artificial leg comprising:
a tibial member having at least one tibial bearing surface, said at least one tibial bearing surface having a first arcuate configuration;
a femoral member being movable relative to said tibial member and having at least one femoral bearing surface, said at least one femoral bearing surface having a second arcuate configuration, said at least one tibial bearing surface supportingly engaging said at least one femoral bearing surface;
a first means for establishing rolling contact between said at least one femoral bearing surface and said at least one tibial bearing surface substantially along the length of each said bearing surface;
a second means for preventing disengagement of said at least one femoral bearing surface and said at least one tibial bearing surface;
means for simulating a patella, said means for simulating being connected to said femoral member and to said tibial member;
brake means for resisting relative movement between said tibial member and said femoral member, said brake means attached anteriorly to said tibial member and said femoral member; and
means for selectively operating said brake means, said means for selectively operating carried by said femoral member.

19. In a prosthetic leg for an above-knee amputee having a femoral member operable for attachment to the amputee's thigh for pivotal movement about a point generally coinciding with the amputee's hip joint, a tibial member with pivotal movement about a prosthetic ankle, a distance defined between said point and said prosthetic ankle, and an angle defined between said femoral member and said tibial member, wherein the improvement comprises:
femoral bearing surface having a first contour;
a tibial bearing surface having a second contour which contacts said femoral bearing surface such that said first contour touches said second contour at an instantaneous axis of rotation;
said angle having a first predetermined value when said femoral member and said tibial member are aligned such that said distance has a first minimum value; and
said first contour and said second contour cooperate to increase said distance when said angle increases, said instantaneous axis of rotation movable posteriorly when said angle increases;
whereby a toggle action is effected to generate stability about said first predetermined value.

20. The prosthetic leg of claim 19 wherein:
said first contour and said second contour cooperate to function as a simple pivot joint when said angle increases above a predetermined angle.

21. A method of walking with a prosthetic knee joint comprising the steps of:
flexing the knee joint with a first range defined between a first predetermined angle and a second predetermined angle which exceeds the first predetermined angle, thereby raising a hip joint of an amputee;
flexing the knee joint within a second range defined between the second predetermined angle and a third predetermined angle which exceeds the second predetermined angle, thereby lowering the hip joint; and
flexing said knee joint through the second range in which the articulation angle exceeds said second predetermined value, thereby establishing a hinged movement.

22. The method of walking of claim 21 wherein:
said flexing within said first range occurs while striking a supporting surface with a prosthetic foot attached below the prosthetic knee joint.

23. The method of walking of claim 22 including the step of:
braking the knee joint against further flexure while in said first range.

24. A prosthetic joint connecting members for relative movement, said joint comprising:
an upper member having means for attachment to an amputee;
a lower member having a prosthetic member connected thereto;
means for swinging lower member relative to said upper member; and
means for rotating said lower member about its longitudinal axis relative to said upper member, being positioned between said lower member and said means for swinging, and having a torsion rod connected at one end to said means for swinging and connected at the other end to said lower member.

25. The prosthetic joint according to claim 24 wherein said means for swinging includes a base, and said means for rotating includes a rotary bearing interposed between said base and said lower member, said bearing being arranged to allow rotation of said base about said longitudinal axis of said lower member, said means for rotating includes means for yieldably resisting rotation of said one member about said longitudinal axis from a predetermined rotational position.

26. The prosthetic joint according to claim 25 wherein said means for rotating includes a torsion rod extending along said longitudinal axis, said rod being secured to said base at a first location on said rod and being secured to said one member at a second location on said rod, said first and second locations being spaced longitudinally along said rod, whereby said rod yieldably resists rotation of said base relative to said one member from a predetermined rotational position.

27. The prosthetic joint according to claim 25 wherein said rotary bearing is a ball bearing and contains grease to dampen torsional motion, and wherein said base and said lower member include stop means to limit rotation relative to each other about said longitudinal axis.

28. A prosthetic knee joint comprising:
a tibial member having at least one tibial bearing surface, said at least one tibial bearing surface having a first arcuate configuration,
a femoral member being movable relative to said tibial member and having at least one femoral bearing surface, said at least one femoral bearing surface having a second arcuate configuration, said at least one tibial bearing surface supportingly engaging said at least one femoral bearing surface;

rolling contact means for establishing rolling contact between said at least one femoral bearing surface and said at least one tibial surface; and engagement means for preventing disengagement of said at least one femoral bearing surface and said at least one tibial bearing surface, said engagement means including a pin connected to one of said tibial member and said femoral member, and the other of said tibial member and said femoral member being provided with a slot for receiving said pin while allowing said pin to move during articulation of the prosthetic knee joint.

29. The prosthetic knee joint of claim 28 further including:

a hinge pin positioned at the posterior end of one of said femoral bearing surface and said tibial bearing surface; and the other of said femoral bearing surface and said tibial bearing surface being provided with a hinge pin receiving socket which cooperates with said hinge pin to permit pivotal movement between said tibial member and said femoral member at the end of rolling contact therebetween.

30. A prosthetic knee joint comprising:

a femoral member having a convex femoral bearing surface and a generally planar upper surface;

a tibial member having a concave tibial bearing surface and a generally planar lower surface;

hypocycloidal means for establishing hypocycloidal motion between said femoral bearing surface and said tibial bearing surface throughout a first range of articulation angles where the articulation angle is defined as one of the intersecting angles between a line normal to the upper surface and a line normal to the lower surface; and pivot means for establishing pivotal motion between said femoral member and said tibial member throughout a second range of articulation angles.

31. The prosthetic knee joint of claim 30 wherein:

the convex femoral bearing surface has a center of curvature; and the hypocycloidal means includes a retaining roller extending laterally from the femoral member and having an axis coincident with the center of curvature;

a guiding roller extending laterally from the femoral member in juxtaposition to the femoral bearing surface and centrally positioned with respect to the arcuate femoral bearing surface, cam surface means carried by the tibial member, positioned above the tibial bearing surface, for cooperation with the retaining roller to maintain contact between the tibial bearing surface and the femoral bearing surface, and guide slot means positioned on the tibial member between the cam surface and the tibial bearing surface for cooperating with the guiding roller to constrain movement between the tibial bearing surface and the femoral bearing surface to substantially hypocycloidal motion.

32. The prosthetic knee joint of claim 31 wherein:

the pivot means includes a pivot roller extending laterally from the femoral member into the guide slot means; and the guide slot means includes a socket portion in which the pivot roller is received to effect transition from the first range of articulation angles to the second range of articulation angles, and an arcuate surface against which the guiding roller moves during the second range of articulation angles to prevent the pivot roller from leaving the socket portion.

33. The prosthetic knee joint of claim 32 further including:

patella means pivotally connected to the femoral member and to the tibial member and having an abutment surface on the patella means to define a limit for the second range of articulation angles.

34. The prosthetic knee joint of claim 32 wherein the pivot means includes:

a pivot roller extending laterally from the femoral member;

guide slot means extending upwardly from the tibial member for receiving the pivot roller throughout the first range of articulation angles and having a socket portion for receiving the pivot roller during the second range of articulation angles; and means for retaining the pivot roller in the socket portion throughout the second range of articulation angles.

* * * * *